United States Patent
Watanabe et al.

(10) Patent No.: US 7,199,264 B2
(45) Date of Patent: Apr. 3, 2007

(54) METHOD OF RESOLVING OPTICAL ISOMERS OF AMINO ACID DERIVATIVE

(75) Inventors: Shin Watanabe, Tsukuba (JP); Mizue Kawahara, Mitsukaido (JP)

(73) Assignee: Tokuyama Corporation, Yamaguchi (JP)

( * ) Notice: Subject to any disclaimer, the term of this patent is extended or adjusted under 35 U.S.C. 154(b) by 430 days.

(21) Appl. No.: 10/415,559

(22) PCT Filed: Oct. 25, 2001

(86) PCT No.: PCT/JP01/09384

§ 371 (c)(1),
(2), (4) Date: May 1, 2003

(87) PCT Pub. No.: WO02/36544

PCT Pub. Date: May 10, 2002

(65) Prior Publication Data

US 2004/0102646 A1    May 27, 2004

(30) Foreign Application Priority Data

Nov. 2, 2000    (JP) .............................. 2000-335352

(51) Int. Cl.
  *C07B 55/00*    (2006.01)
(52) U.S. Cl. .................................................... 562/401
(58) Field of Classification Search ................. 562/401
  See application file for complete search history.

(56) References Cited

U.S. PATENT DOCUMENTS 5,578,212 A * 11/1996 Pirkle et al. ................. 210/638

OTHER PUBLICATIONS

Li et al., Journal of Chromatography, 1992, 625: 109-120.*

S. Li et al., "Direct separation of enantiomers using multiple-interaction chiral stationary phases based on the modified β-cyclodextrin-bonded stationary phase", Journal of Chromatography, vol. 625, No. 2, pp. 109-120, 1992.
T. Takeuchi et al., "Enantiomeric Resolution of Dansyl Amino Acids by Micro High-Performance Liquid Chromatography with β-Cyclo-Dextrin Inclusion Complexes ", Journal of Chromatography, vol. 357, pp. 409-415, 1986.
S. C. Chang et al., "Facile Resolution of N-tert-Butoxy-Carbonyl Amino Acids: The Importance of Enantiomeric Purity in Peptide Synthesis", Journal of Liquid Chromatography, vol. 15, No. 9, pp. 1411-1429, 1992.
C. Pettersson, "Chromatographic Separation of Enantiomers of Acids with Quinine as Chiral Counter Ion", Journal of Chromatography, vol. 316, pp. 553-567, 1984.
S. C. Chang et al., "Facile Resolution of N-tert-Butoxy-Carbonyl Amino Acids:" The Importance of Enantiomeric Purity in Peptide Synthesis, Journal of Liquid Chromatography, 1992, vol. 15, No. 9, pp. 1411-1429, especially pp. 1423 and 1424.

* cited by examiner

*Primary Examiner*—Joseph K. McKane
*Assistant Examiner*—Robert Shiao
(74) *Attorney, Agent, or Firm*—Wenderoth, Lind & Ponack, L.L.P.

(57) ABSTRACT

Provided is a separating method for an optical isomer mixture comprising the steps of mixing an amino acid derivative such as N-(tert-butoxycarbonyl)-DL-alanine in which optical isomers of a D type and an L type are present in a mixture with a hydrophilic compound such as β-cyclodextrin having a different affinity to two kinds of the optical isomers described above and then bringing the resulting aqueous solution or aqueous suspension into contact with a hydrophobic substance such as a solid matter subjected on a surface thereof to hydrophobic treatment on the condition that the pH is 3.5 or lower or under the coexistence of ions including an atomic group having hydrophobicity which can be a counter ion for the amino acid derivative described above such as a triethylammonium ion to thereby separate the D type amino acid derivative from the L type amino acid derivative present in the above aqueous solution or aqueous suspension.

14 Claims, No Drawings

METHOD OF RESOLVING OPTICAL ISOMERS OF AMINO ACID DERIVATIVE

This application is a U.S. national stage of International Application No. PCT/JP01/09384 filed Oct. 25, 2001.

TECHNICAL FIELD

The present invention relates to a method of separating the respective isomers from a mixture comprising a pair of optical isomers of an amino acid derivative.

BACKGROUND ART

An amino acid derivative in which a hydrogen atom in an amino group of amino acid is substituted or protected by an alkoxycarbonyl group such as tert-butoxycarbonyl, an aralkyloxycarbonyl group, an aryloxycarbonyl group, an alkenyloxycarbonyl group or an acyl group is an important compound as a medicine or a medicinal intermediate. In these amino acid derivatives, optical isomers are present in many cases, and it is widely known that a large difference in a physiological activity and a toxicity thereof is frequently present between these optical isomers. Accordingly, it is very important in amino acid derivatives used in such fields to produce the products having a high optical purity and confirm the optical purity prior to use thereof.

In general, optical isomers can be separated and refined by means of liquid chromatography, and various columns for separating optical isomers in which polysaccharides or amino acid derivatives are carried on silica gel have been developed.

Introduced in, for example, Takeuchi et al., Journal of Chromatography, 357 (1986), p. 409 to 415 is an example in which α-cyclodextrin and β-cyclodextrin are used as a mobile phase component in separating racemic mandelic acid and a racemic mandelic acid derivative, and it is introduced therein that a stationary phase in which cyclodextrin is bonded for high performance (or high speed) liquid chromatography (HPLC) is applied for separating optical isomers, geometrical isomers and structural isomers.

Besides, the authors of the literature have reported separation of enantiomers of dansyl amino acid carried out by micro HPLC in which β-cyclodextrin is used as a mobile phase component. The separating method described in the above publication makes use of the character that β-cyclodextrin is liable to make a complex (clathrate complex) with a low molecular compound having a naphthalene ring which constitutes a dansyl group, and the above separating method can not be applied as it is to separation of optical isomers of an amino acid derivative having no naphthalene ring. For example, it is explained in the above literature that the higher the pH of a mobile phase becomes, the larger the separation factor tends to grow and that the vicinity of pH 6 is the most preferred. However, it would be impossible to separate the optical isomers of the amino acid derivative described above having tert-butoxycarbonyl in such pH region.

An optical isomer of an amino acid derivative in which a dansyl group is introduced into an amino group of amino acid can be separated by the method of Takeuchi et al. described above, but it is not necessarily easy in a certain case to remove the dansyl group and allow the amino acid derivative to be back to the original amino acid. Accordingly, still strongly required to be provided is a method for separating an amino acid derivative which can be used as a synthetic intermediate for medicines, for example, physiologically active peptide and which is a group (refer to, for example, tert-butoxycarbonyl described above) introduced for such use and/or separation and capable of being easily removed after a prescribed purpose is achieved.

DISCLOSURE OF THE INVENTION

The present inventors have made various investigations in order to meet the requirement described above considering that if the amino acid derivative described above containing a pair of D type and L type optical isomers is allowed to be coexistent with a hydrophilic compound having a different affinity to the respective optical isomers making use of this difference might make it possible to separate both. As a result thereof, they have found that satisfactory separation can not be carried out only by treating an amino acid derivative having substituents including tert-butoxycarbonyl described above with β-cyclodextrin according to the method of Takeuchi et al., but the respective optical isomers can efficiently be separated from each other by bringing an optical isomer mixture into contact with a hydrophobic compound in the coexistence of a fixed hydrophilic compound having a different affinity to a pair of the respective optical isomers including β-cyclodextrin under such a specific condition as elevating a hydrophobicity of a complex which is anticipated to be produced. Thus, they have come to complete the present invention.

Hence, according to the present invention, provided is a method for separating the respective optical isomers from a mixture containing a pair of optical isomers of an amino acid derivative in which one of hydrogen atoms of an amino group or an imino group of amino acid having at least one asymmetric carbon is N-substituted with an organic carbonyl group, and the above separating method comprises the steps of:

(A) preparing the above mixture,
(B) mixing the above mixture with a hydrophilic compound having a different affinity to the respective optical isomers contained therein in an aqueous solution to form a complex,
(C) placing an aqueous solution or an aqueous suspension containing the above complex to:
  (i) the condition that the pH is 3.5 or lower or
  (ii) the coexistence thereof with a compound having a group which can be a counter ion for an ion originating in a charging group of the above amino acid derivative and a hydrophobic atomic group, whereby a difference in hydrophobicity is brought about between the respective optical isomers and
(D) separating the respective optical isomers from each other making use of such difference in the hydrophobicity.

Further, according to the present invention, provided as well are a production process for a high purity optical isomer of amino acid or a derivative thereof using such separating method and use of the above separating method for efficiently carrying out such production process.

BEST MODE FOR CARRYING OUT THE INVENTION

The amino acid derivative to which the method of the present invention is applied may be any derivative as long as it brings about a difference in hydrophobicity between the respective optical isomers (or between complexes formed from the respective optical isomers) when passing through an action and an effect provided by the present invention, for example, the steps (B) and (C). "A pair of optical isomers" used in the present invention means an optical isomer comprising, for example, an L type and a D type of specific amino acid.

The action and an effect described above shall not be restricted by a theory, and it is supposed that according to the present invention, the following mechanism makes it possible to separate the respective optical isomers from a pair of optical isomers. For example, when an amino acid derivative containing the optical isomers of a D type and an L type coexists with a hydrophilic compound having the property described above in an aqueous solution, the optical isomer having a strong affinity to the above hydrophilic compound causes an interaction in any form to become a complex (a clathrate complex and a molecular aggregate bonded by virtue of the other physical or chemical interaction) having a higher hydrophilicity than that of the other optical isomer, but even if they are brought into contact with a hydrophobic substance, both can not be separated because a difference in an affinity (for example, an adsorptive strength) to the above hydrophobic substance between both is not sufficiently large. On the other hand, when a pH of the aqueous solution is set to 3.5 or lower, a carboxyl group of the amino acid derivative stays undissociated, and therefore further elevated is a hydrophobicity of the optical isomer in which hydrophobicity grows relatively higher (that is, the optical isomer which does not form a complex with the hydrophilic compound or which is considered to form a more unstable complex than the complex described above). However, the hydrophilic compound has a large effect in the complex described above and is not different so much in a hydrophilicity thereof, so that an equilibrium distribution factor of both to the hydrophobic substance is changed, and it is considered that the result thereof has made it possible to separate the optical isomers at a good efficiency. Further, when ions including an atomic group having hydrophobicity are contained therein, the hydrophobicity is elevated because even if a carboxyl group of the optical isomer in which hydrophobicity grows relatively higher is dissociated, it forms an ion pair with the above ions. On the other hand, the optical isomer in the more stable complex can not form such ion pair because of the presence of the hydrophilic compound in the vicinity thereof, or the effect of the counter ion is weakened, and the equilibrium distribution factor to the hydrophobic substance is changed similarly to the case described above. Thus, it is supposed that the separation of the optical isomers has become possible.

Accordingly, in the respective structures of the present invention described below in details, the structures which are suited for providing the action described above shall be selected.

The N-substituted amino acid derivative which is used or a target for treating in the present invention is represented by Formula (I):

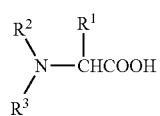
(I)

and the examples of the respective groups in the formula described above shall be given below while describing together typical amino acids with common names in a parenthesis.

$R^1$ represents a non-substituted or substituted $C_{1-6}$ alkyl group, and the substituent applied when substituted is selected from the group consisting of hydroxy (serine and threonine), mercapto (cysteine), methylthio (methionine), amino (lysine), mono- or dimethylamino, $C_{1-6}$ alkyl, $C_{1-6}$ alkylcarbonylamino, $C_{1-6}$ alkyloxycarbonyl, amidinoamino (arginine), carboxy (glutamic acid and aspartic acid), $C_{1-6}$ alkyloxycarbonyl, carbamoyl (glutamine and asparagine), non-substituted or substituted phenyl [the case of non-substituted phenyl (phenylalanine), and the substituents in the case of substituted phenyl are the same or different and can be 1 to 3 halogen atoms, hydroxy (tyrosine), mercapto, methyl, trifluoromethyl or amino] and a 5-membered cyclic group (histidine and tryptophan) which has 1 to 2 cyclic nitrogen atoms and which may be condensed with a benzene ring.

Alanine, isoleucine, leucine and valine are included in typical raw material amino acid (or called basic amino acid) when $R^1$ is a non-substituted $C_{1-6}$ alkyl group.

One of $R^2$ and $R^3$ is a hydrogen atom, and the other represents alkoxycarbonyl, aralkyloxycarbonyl, aryloxycarbonyl, alkenyloxycarbonyl or acyl, or a group representing a hydrogen atom in $R^2$ and $R^3$ represents, in place of a hydrogen atom, propane-1,3-diyl (proline), 2-hydroxypropane-1,3-diyl or 1-hydroxypropane-1,3-diyl which can be combined with $R^1$ to form a 5-membered ring via a nitrogen atom they are bonded to.

The method of the present invention is suitably applied to those, among the amino acid derivatives thus specified, originating in alanine, proline, leucine, isoleucine, valine, tryptophan, phenylalanine, tyrosine, serine, methionine, glutamine, glutamic acid and lysine.

Alkyl described in the present specification including the compound of Formula (I) described above and alkyls in alkoxy or alkyloxy, alkoxycarbonyl and alkylcarbonyl have carbon atoms described respectively and can be linear or branched alkyls, and they shall not be restricted and are selected from methyl, ethyl, propyl, iso-propyl, n-butyl, sec-butyl, iso-butyl, tert-butyl, n-pentyl, octyl, dodecyl and octadecyl.

On the other hand, $C_{1-4}$ alkylene contained in aralkyl, preferably phenyl-$C_{1-4}$ alkylene includes methylene, ethylene, propylene, 2-methylpropylene and butylene. Alkenyl contained in alkenyloxycarbonyl is preferably $C_{3-9}$ alkenyl and shall not be restricted, and it includes 1-butene and 2-butene.

The same or different maximum three substituents can be present on a benzene ring contained in aralkyloxycarbonyl, aryloxycarbonylaryl and benzoyl which are described in the present specification, and such substituents shall not be restricted and can include a halogen atom (fluorine, chlorine, bromine and iodine), hydroxy, mercapto, methyl, trifluoromethyl, amino and nitro.

In the separating method of the present invention, treated is any pair of the optical isomer mixtures in the amino acid derivatives in which at least one of hydrogen atoms in an amino group of the amino acids described above is substituted with an alkoxycarbonyl group, an aralkyloxycarbonyl group, an aryloxycarbonyl group, an alkenyloxycarbonyl group or an acyl group. To be typical, the D isomer or the L isomer is separated from an amino acid derivative in which D type and L type optical isomers (hereinafter referred to simply as a D isomer and an L isomer) of some amino acid derivative are present in a mixture. Any one of the D isomer and the L isomer which are present in a mixture may be markedly more (90 to 99.9%) than the other or the D isomer and the L isomer may be present in a mixture in the same amount like as racemate. The separating method of the present invention can be applied as well to separation of the optical isomers of an amino acid derivative having two or more asymmetric carbons, but from the viewpoint of the high separation efficiency, it is suitably used for an amino acid derivative in which the presence of one asymmetric carbon allows two kinds of optical isomers to be present.

The specific examples of an N-substituent of the N-substituted amino acid derivative which is treated by the method of the present invention shall not be restricted and are suitably the following groups from the viewpoints of the separability and the usefulness of the amino acid derivative itself. That is, the alkoxycarbonyl group is suitably a group having the whole carbon number of 2 to 10 such as methoxycarbonyl, ethoxycarbonyl, n-propoxycarbonyl, isopropoxycarbonyl, tert-butoxycarbonyl, isobutoxycarbonyl and tert-amyloxycarbonyl. The aralkyloxycarbonyl group is suitably a group having the whole carbon number of 8 to 15 such as benzyloxycarbonyl, p-nitrobenzyloxycarbonyl, p-methoxybenzyloxycarbonyl and p-fluorenylmethoxycarbonyl. The aryloxycarbonyl group is suitably a group having the whole carbon number of 7 to 10 such as phenyloxycarbonyl, m-nitrophenyloxycarbonyl, p-methylphenyloxycarbonyl, m-methylphenyloxycarbonyl, 2,4-dimethylphenyloxycarbonyl and 2,4,6-trimethylphenyloxycarbonyl. The alkenyloxycarbonyl group is suitably a group having the whole carbon number of 4 to 10 such as 1-buteneoxycarbonyl and 2-buteneoxycarbonyl. Further, the acyl group is suitably a group having the whole carbon number of 1 to 7 such as formyl, acetyl, propanoyl, butanoyl and benzoyl.

Among these substituents, methoxycarbonyl, ethoxycarbonyl, tert-butoxycarbonyl, tert-amyloxycarbonyl, benzyloxycarbonyl, phenyloxycarbonyl, formyl, acetyl, propanoyl or benzoyl is particularly preferred because the particularly high separation can be expected.

To specifically show the amino acid derivative suitably used in the separating method of the present invention, it includes amino acid derivatives substituted with an alkoxycarbonyl group, such as N-(tert-butoxycarbonyl)-alanine, N-(tert-butoxycarbonyl)-proline, N-(tert-butoxycarbonyl)-leucine, N-(tert-butoxycarbonyl)-isoleucine, N-(tert-butoxycarbonyl)-valine, N-(tert-butoxycarbonyl)-tryptophan, N-(tert-butoxycarbonyl)-phenylalanine, N-(tert-butoxycarbonyl)-serine, N-(tert-butoxycarbonyl)-methionine, N-(tert-butoxycarbonyl)-glutamine, N-(tert-butoxycarbonyl)-glutamic acid, N-(tert-butoxycarbonyl)-lysine and N-(tert-butoxycarbonyl)-tyrosine; amino acid derivatives substituted with an aralkylcarbonyl group, such as N-benzyloxycarbonyl-alanine, N-benzyloxycarbonyl-proline, N-benzyloxycarbonyl-leucine, N-benzyloxycarbonyl-isoleucine, N-benzyloxycarbonyl-valine, N-benzyloxycarbonyl-tryptophan, N-benzyloxycarbonyl-phenylalanine, N-benzyloxycarbonyl-serine, N-benzyloxycarbonyl-methionine, N-benzyloxycarbonyl-glutamine, N-benzyloxycarbonyl-glutamic acid and N-benzyloxycarbonyl-lysine; amino acid derivatives substituted with an aryloxycarbonyl group, such as N-phenyloxycarbonyl-alanine, N-phenyloxycarbonyl-proline, N-phenyloxycarbonyl-leucine, N-phenyloxycarbonyl-isoleucine, N-phenyloxycarbonyl-valine, N-phenyloxycarbonyl-tryptophan, N-phenyloxycarbonyl-phenylalanine, N-phenyloxycarbonyl-serine, N-phenyloxycarbonyl-methionine, N-phenyloxycarbonyl-glutamine, N-phenyloxycarbonyl-glutamic acid and N-phenyloxycarbonyl-lysine; and amino acid derivatives substituted with an acyl group such as N-benzoyl-alanine, N-benzoyl-proline, N-benzoyl-leucine, N-benzoyl-isoleucine, N-benzoyl-valine, N-benzoyl-tryptophan, N-benzoyl-phenylalanine, N-benzoyl-serine, N-benzoyl-methionine, N-benzoyl-glutamine, N-benzoyl-glutamic acid and N-benzoyl-lysine. Among them, the compounds having one asymmetric carbon in a molecule are particularly suitably used.

The mixture containing a pair of the optical isomers of the N-substituted amino acid derivative treated by the method of the present invention may be produced by any process. For example, capable of being an object for treatment (a mixture of optical isomers or a non-separated amino acid derivative) in the method of the present invention is a compound obtained by reacting amino acid (called raw material amino acid or basic amino acid) represented by, for example, Formula (I-a):

(wherein $R^1$ is the same as the definition in Formula (I) described above, and $R^{2-a}$ and $R^{3-a}$ are independently a hydrogen atom or can represent propane-1,3-diyl, 2-hydroxypropane-1,3-diyl or 1-hydroxypropane-1, 3-diyl which can form a 5-membered ring via a nitrogen atom they are bonded to by combining any one of them with $R^1$) with an active ester (for example, di-tert-butyl carbonate, chloroformic acid esters and acyl halides) of an acid represented by Formula (II):

(wherein A represents alkoxy, aralkyloxy, aryloxy, alkenyloxy or alkyl or aryl) in a solvent exerting no adverse effect on the reaction in the presence of a base. Usually, when such organic chemical synthetic reaction is used to synthesize an amino acid derivative, a racemization or a compound having an optical purity of 80 to 99% is obtained in a certain case even when raw material amino acid having a high optical purity is used.

In the separating method of the present invention, a hydrophilic compound (hereinafter referred to as a chiral selector) having a different affinity to the respective optical isomers (a D isomer and an L isomer) contained in a non-separated amino acid derivative is mixed with the above non-separated amino acid derivative in an aqueous solution, and then the resulting aqueous solution or aqueous suspension is brought into contact with a hydrophobic substance under such condition that the pH is 3.5 or lower or under the coexistence of ions including an atomic group having hydrophobicity which can be a counter ion for the amino acid derivative described above (it is placed thereunder to thereby bring about a difference in hydrophobicity between the respective optical isomers) to separate the respective optical isomers (the D type amino acid derivative and the L type amino acid derivative) present in the aqueous solution or the aqueous suspension.

A publicly known compound can be used as the chiral selector without setting specific restrictions as long as it is a hydrophilic compound having a different affinity to the respective optical isomers. In general, an optically active compound and a host compound having a chiral cavity or space (a compound which can include the other compounds and ions in an inside to form a clathrate compound) have a different affinity to the respective optical isomers (the D isomer and the L isomer), and therefore among such compounds, the hydrophilic compounds can suitably be used as the chiral selector in the present invention. In the present specification, the hydrophilicity means that solubility is shown, though merely slight, in water. When the chiral selector is hydrophobic, the D isomer can not efficiently be separated from the L isomer.

A compound which can be used as the chiral selector in the present invention includes polysaccharides and the derivatives thereof and natural optically active compounds of amino acids and the derivatives thereof, and the specific examples of these compounds include the following compounds.

That is, shown as the examples of the polysaccharides are amylose, α-cyclodextrin, β-cyclodextrin and γ-cyclodextrin. Shown as the examples of the polysaccharide derivatives are cyclodextrin derivatives such as heptakis(2,6-O-dimethyl)-β-cyclodextrin, heptakis(2,3,6-O-trimethyl)-β-cyclodextrin, heptakis(2,6-O-hydroxypropyl)-β-cyclodextrin, heptakis(2,3,6-O-hydroxypropyl)-β-cylclodextrin, heptakis(2,6-O-methyl-3-O-acetyl)-β-cyclodextrin, hexakis(2,6-O-dimethyl)-β-cyclodextrin, hexakis(2,3,6-O-trimethyl)-β-cyclodextrin, hexakis(2,6-O-hydroxypropyl)-β-cyclodextrin, hexakis(2,3,6-O-hydroxypropyl)-β-cyclodextrin, hexakis(2,6-O-methyl-3-O-acetyl)-β-cyclodextrin, octakis(2,6-O-dimethyl)-β-cyclodextrin, octakis(2,3,6-O-trimethyl)-β-cyclodextrin, octakis(2,6-O-hydroxypropyl)-β-cyclodextrin, octakis(2,3,6-O-hydroxypropyl)-β-cyclodextrin and octakis(2,6-O-methyl-3-O-acetyl)-β-cyclodextrin. Phenylalanine, tryptophan and leucine are shown as the examples of the natural optically active compounds of amino acids, and shown as the examples of the derivatives thereof are N-(tert-butoxycarbonyl)-L-tryptophan, N-(tert-butoxycarbonyl)-D-tryptophan, N-(tert-butoxycarbonyl)-L-phenylalanine, N-(tert-butoxycarbonyl)-D-phenylalanine, N-(tert-butoxycarbonyl)-L-leucine and N-(tert-butoxycarbonyl)-D-leucine. These compounds may be used alone or in combination of two or more kinds thereof.

In the present invention, among the chiral selectors described above, various cyclodextrins or the derivatives thereof are suitably used because of a high separating capacity thereof. Cyclodextrins in which a part of hydroxyl groups or hydrogen atoms is substituted with hydroxylethyl, hydroxylpropyl, trifluoroacetyl or acetyl are suitably used as cyclodextrin derivatives from the viewpoints of availability, a solubility in water and a separability.

An amount of the chiral selector used in the present invention may suitably be decided according to an amount of the non-separated amino acid derivative used and an optical purity thereof so that a sufficiently large amount of the chiral selector is used as compared with that of the D isomer or the L isomer having affinity. It is suitably used in a range of 1 mM to 100 mM from the viewpoints of obtaining the satisfactory separation efficiency and preventing a reduction in the operability caused by excess use and a rise in the viscosity.

In the separating method of the present invention, the non-separated amino acid derivative is mixed with the chiral selector described above in an aqueous solution in order to improve contact of the chiral selector with the D isomer or the L isomer contained in the non-separated amino acid derivative and obtain the high separation efficiency. In this case, the aqueous solution means a solution containing water, that is, water or a mixed solution of water and an organic compound having a solubility in water, and the mixed solution of water and the organic compound is suitably used in order to efficiently bring about the interaction of the D isomer or the L isomer contained in the non-separated amino acid derivative with the chiral selector and obtain the high separation efficiency. The organic compound used in this case shall not specifically be restricted as long as it has miscibility with water and includes nitrile compounds such as acetonitrile; aliphatic alcohols such as methanol, isopropyl alcohol, propyl alcohol, ethanol, butyl alcohol, tert-butyl alcohol and octanol; aromatic alcohols such as phenol; ethylene glycol, glycerol and water soluble polymers such as polyethylene glycol and polyvinyl alcohol. Among them, acetonitrile, methanol, isopropyl alcohol and ethanol each having a low boiling point are suitably used from the viewpoint of easiness in removing after separating the optical isomers. A use amount of the organic compound shall not specifically be restricted and is suitably 0.01 to 50 mass %, particularly 0.1 to 25 mass % based on the total mass of water and the above organic compound.

A method for mixing the non-separated amino acid derivative with the chiral selector in the aqueous solution shall not specifically be restricted, and the prescribed amounts of the non-separated amino acid derivative and the chiral selector each are weighed and added simultaneously or in order to the aqueous solution, followed by stirring and mixing them. In this case, an amount ratio of the non-separated amino acid derivative to the chiral selector shall not specifically be restricted as long as it is such an amount that a mole number of the chiral selector is more than a mole number of the optical isomer having a high affinity to the chiral selector contained in the non-separated amino acid derivative, and a ratio {(mole number of the chiral selector)/(mole number of the D isomer and mole number of the L isomer) of a mole number of the chiral selector to a mole number of the non-separated amino acid derivative (that is, the total of the D isomer and the L isomer) is suitably 1000 to 1, particularly 100 to 5 from the viewpoint of a rise in the separation efficiency.

In the separating method of the present invention, the aqueous solution or the aqueous suspension prepared in the manner described above containing the non-separated amino acid derivative and the chiral selector has to be brought into contact with the hydrophobic substance (i) under the condition that a pH thereof is 3.5 or less or (ii) in the existence of "ions including an atomic group having hydrophobicity" (hereinafter referred to as a hydrophobic counter ion) which can be a couter ion for the amino acid derivative. When it is brought into contact with the hydrophobic substance without satisfying the condition of (i) or (ii), the good separation efficiency is not obtained, though it is supposed to be attributable to the fact that an effective difference is not produced in hydrophobicity between the D isomer and the L isomer.

In order to satisfy the condition of (i) described above, a pH controlling agent may be used to control a pH of the aqueous solution or the aqueous suspension to 3.5 or less. The pH controlling agent which can be used in this case shall not specifically be restricted as long as a pH of the aqueous solution can be controlled to 3.5 or less, and capable being used without having restrictions are mineral acids such as phosphoric acid, sulfuric acid and hydrochloric acid; and organic acids such as formic acid, acetic acid, lactic acid, propionic acid, citric acid, maleic acid and malonic acid. A concentration of these pH controlling agents shall not specifically be restricted, and it is used usually in a range of 1 to 100 mM, suitably 1 to 30 mM. A pH of the aqueous solution or the aqueous suspension is suitably controlled to 1 to 3, particularly 1.4 to 2.5 from the viewpoint of a rise in the separation efficiency. The pH is advisably controlled before brought into contact with the hydrophobic substance or may be controlled before mixing the non-separated amino acid derivative with the chiral selector. In such mixing, the temperature shall not be restricted as long as mixing is sufficiently carried out, and it is advisably carried out usually at 10 to 30° C.

The hydrophobic counter ions which are allowed to coexist when brought into contact with the hydrophobic substance on the condition of (i) described above shall not specifically be restricted as long as they are present in the form of ions having a charge reverse thereto to form an ion pair when an ionizable part such as a carboxyl group in the amino acid derivative is ionized in the aqueous solution. The "atomic group having hydrophobicity" present in the hydrophobic counter ions means an atomic group having a function of increasing a hydrophobicity of a $C_{1-22}$ alkyl group such as methyl, ethyl, isopropyl, butyl, tert-butyl, octyl, dodecyl and octadecyl; and an aryl group such as phenyl and naphthyl. These atomic groups may have hydrophobicity as a whole and may have a functional group such as a hydroxyl group and a nitro group and a halogen atom such as fluorine, chlorine, bromine and iodine in a part thereof.

The hydrophobic counter ion is used by adding to the aqueous solution in the form a compound (hereinafter referred to as a hydrophobic counter ion-forming compound) which is ionized in an aqueous solution to form a cation or an anion. Capable of being used as such compound are amine compounds, ammonium compounds, boron compounds, phosphorus compounds and sulfonic acid compounds each having the atomic group described above having hydrophobicity. The amine compounds are neutral and therefore have to be present in the form of a cation by adding a hydrogen ion in an aqueous solution. Accordingly, they are used controlling a pH of the aqueous solution to not higher than a pKa of the amine compounds used.

To show the examples of the compounds providing the hydrophobic counter ion which can be used in the present invention, the amine compounds include trimethylamine, diethylamine, triethylamine, triethanolamine, triisopropylamine, diisopropylmethylethanolamine, tributylamine, dibutylamine, butylamine, octylamine, dioctylamine, trioctylamine, diphenylamine and triphenylamine.

The ammonium compounds include ammonium salts such as hydrochlorides, hydrobromides and hydroxides of these amine compounds and in addition thereto, tetramethylammonium chloride, tetramethylammonium bromide, tetraethylammonium chloride, tetraethylammonium bromide, tetrabutylammonium chloride, tetrabutylammonium bromide and tetrabutylammonium hydroxide.

The boron compounds include ionic boron compounds such as sodium tetraphenylborate and sodium tetra(chlorophenyl)borate; the phosphorus compounds include tetrapheylphosphine chloride and tetraocteylphosphine chloride; and the sulfonic acid compounds include toluenesulfonic acid, octylsulfonic acid and dodecylsulfonic acid.

Among these compounds, triethylamine, triethanolamine, tributylamine, dibutylamine, tributylamine, tetrabutylamine, tetraamylamine and dodecylsulfonic acid are suitably used from the viewpoint of a solubility in the aqueous solution.

An amount of the hydrophobic counter ion described above shall not specifically be restricted as long as it is a sufficiently large amount for the isomer having a lower affinity to the chiral selector among the D isomer or the L isomer contained in the non-separated amino acid derivative, and the optimum amount may suitably be decided from the viewpoint of the separation efficiency according to the kind and the amount of the non-separated amino acid derivative and the kind of the chiral selector. It is used in an amount falling in a range of usually 0.01 to 50 mM, particularly 0.1 to 30 mM in terms of a concentration in the aqueous solution or the aqueous suspension.

A pH of the hydrophobic counter ion described above shall not specifically be restricted as long as it is a pH area in which the non-separated amino acid derivative being an object for separation can be ionized to form an ion pair with the hydrophobic counter ion, and taking an easiness in controlling a pH of a buffer solution and an easiness in treating a waste liquid after use into consideration, it falls suitably in a range of pH=4 to 8, particularly pH=4 to 7. Capable of being used in order to control the pH to such range are the inorganic acids and the organic acids each described above and in addition thereto, alkaline salts such as sodium hydroxide, potassium hydroxide, calcium hydroxide, sodium carbonate, potassium carbonate and calcium carbonate, salts such as sodium hydrogenphospate and potassium dihydrogenphospate and organic compounds for a pH buffer solution such as tris(hydroxymethyl)aminomethane, 4-(2-hydroxyethyl)-1-piperazineethanesulfonic acid and morpholinepropanesulfonic acid.

Addition of the compound providing the hydrophobic counter ion and pH control thereof carried out if necessary may be carried out before brought into contact with the hydrophobic substance and may be carried out as well before mixing the non-separated amino acid derivative with the chiral selector.

Further, salts for controlling the ionic strength or "compounds having an absorption spectrum in a ultraviolet region and a visible region" for making it easy to detect the D isomer and the L isomer when applying the separating method of the present invention to an optical purity analytical method can be added as an optional component to the aqueous solution or the aqueous suspension described above which is brought into contact with the hydrophobic substance. In this case, sodium chloride, potassium chloride and calcium chloride can be used as the salts, and organic compounds having an aromatic ring such as toluenesulfonic acid, sodium toluenesulfonate, sodium benzenesulfonate, sodium naphthalenesulfonate, fluorescein, phenolphthalein, Nile Blue, eosin and coumarin can be used as the "compounds having an absorption spectrum in a ultraviolet region and a visible region".

In the separating method of the present invention, "the aqueous solution or the aqueous suspension containing the non-separated amino acid derivative and the chiral selector is brought into contact with the hydrophobic substance under a condition satisfying the condition of (i) or (ii) described above to separate the D isomer from the L isomer making use of a difference in an affinity thereof to the above hydrophobic substance.

The hydrophobic substance used in this case shall not specifically be restricted as long as it is a substance which has a higher hydrophobicity than that of the aqueous solution described above and which can readily be separated from it, and a liquid or solid hydrophobic substance is used. Capable of being used as the liquid hydrophobic substance are, for example, organic solvents which are insoluble or scarcely soluble in water such as chloroform, dichloromethane, hexane and octanol. Solid matters having a hydrophobic surface can be used as the solid hydrophobic substance without having specific restrictions. To give the examples of such substance, capable of being given are solid matters obtained by bonding compounds having a hydrophobic group having one or more carbon atoms such as octadecyl, octyl, butyl, methyl, phenyl and cyanopropyl on the surface of inorganic fine particles of silica or, titania; solid matters obtained by adsorbing or bonding hydrophobic polymers such as polystyrene, silicone and polymethyl methacrylate on the surface of inorganic fine particles of silica or titania; fine particulate solid matters of polymers having hydrophobicity such as polystyrene and polymethyl methacrylate; and solid matters obtained by bonding compounds having a hydrophobic group having one or more carbon atoms such as octadecyl, octyl, butyl methyl, phenyl and cyanopropyl on the surface of polymers such as polystyrene and polymethyl methacrylate. Capable of being used as well in order to adjust the hydrophobicity are those obtained by further bonding, if necessary, compounds having an ion exchange group such as a sulfonyl group, an amino group and an ammonium group on the surface of these solid matters. When using the solid hydrophobic substance, the larger the surface area is, the more the amount of the amino acid derivative which can be separated at one time grows, and therefore a solid fine particle having a hydrophobic surface is preferably used.

In the separating method of the present invention, a method for bringing the aqueous solution or the aqueous suspension containing the non-separated amino acid derivative (a mixture of the respective optical isomers) and the chiral selector into contact with the hydrophobic substance to separate the D isomer from the L isomer shall not specifically be restricted, and it can suitably be carried out by the following method.

That is, a solid hydrophobic substance is filled into a hollow tube, and it is used as a separating column for chromatography, whereby optical isomers can be separated. In this case, the aqueous solution containing the chiral selector as a mobile phase and satisfying the condition of (i) or (ii) described above is allowed to flow through the separation column, and the non-separated amino acid derivative is injected into the upper stream of the separation column to carry out liquid chromatography. The non-separated amino acid derivative is mixed with the chiral selector in the aqueous solution in the column and brought into contact with the hydrophobic substance which is a filler in the column, and after a fixed time passes, the respective optical isomers flow out from the downstream of the separating column in the state that the optical isomers are separated (in other word, in a different retention time). UV absorption in a specific wavelength, an electric conductivity and a refractive index in the flowing-out mobile phase are observed with the passage of time, whereby a chromatograph can be obtained. Flowing out of the D isomer and the L isomer is detected from the above chromatograph, and they are fractioned, whereby the amino acid derivative of the present invention having an improved optical purity can be obtained. The method carried out by the above liquid chromatography is easy in operation and has a high separating performance, and therefore it is the particularly suited embodiment as the separating method of the present invention.

Further, the non-separated amino acid derivative is mixed in advance with the chiral selector in an aqueous solution, and then the aqueous solution or the aqueous suspension which is prepared so that the condition of (i) or (ii) described above is satisfied (the aqueous solution or the aqueous suspension which is prepared in such manner shall be referred to as a prepared aqueous solution or aqueous suspension) is brought into contact with the hydrophobic substance, whereby the D isomer can be separated as well from the L isomer.

For example, when a liquid is used as the hydrophobic substance, the prepared aqueous solution and the hydrophobic substance are introduced into a vessel and stirred by means of a stirrer or by vigorously shaking when the vessel is of a structure in which it can tightly be closed like a separating funnel. Then, the is liquid was left standing to separate into two layers, and the liquids in two layers are separately recovered, whereby they can be separated. In this case, distribution is made in a proportion according to the characteristic of the chiral selector used so that the optical isomer (or the complex thereof) having a strong hydrophobicity is present more in the hydrophobic layer and the optical isomer (or the complex thereof) having a strong hydrophilicity is present more in the hydrophilic layer, and the D isomer or the L isomer is concentrated in each layer. When the D isomer or the L isomer having a satisfactory optical purity is not obtained by this concentration, the liquid is removed by distillation under reduced pressure from one layer separated and recovered by the operation described above, and then the same separating operation is repeated again, whereby the D isomer or the L isomer having a high optical purity can be obtained.

Also, when a solid matter is used as the hydrophobic substance, the solid hydrophobic substance is added and brought into contact with the prepared aqueous solution by stirring, and the solid hydrophobic substance is removed by filtering after a fixed time passes to recover the liquid component, whereby the separation can be carried out. In this case, the optical isomer (or the complex thereof) having a strong hydrophobicity is adsorbed more onto the solid hydrophobic substance, and therefore the optical isomer (or the complex thereof) having a strong hydrophilicity is present more in the filtrate. When the satisfactory separation can not be carried out by one operation, the liquid is removed from the filtrate by distillation under reduced pressure similarly to the case described above, and then the same separating operation is repeated again, whereby the D isomer or the L isomer having a high optical purity can be obtained. It is a matter of course that the optical isomer adsorbed onto the solid hydrophobic substance is washed with a hydrophobic organic solvent and the washing liquid is recovered and that the solvent is removed from the recovered liquid, whereby the other optical isomer can be recovered. Also in this case, the purity can be raised by repeating the operation.

The optical isomer separated by the separating method of the present invention is obtained usually in the form of a solution or a suspension containing impurities (the chiral selector used for separation, various salts and the like) in many cases, and it is a matter of course that the amino acid derivative having an improved optical purity can be isolated from these solutions. Various methods can be used for such isolating method, and one example thereof includes a method in which a liquid component is removed by distillation under reduced pressure and then a solvent dissolving the amino acid derivative but not dissolving the other impurities is added to dissolve only the amino acid derivative and in which the impurities are separated by filtering and then the solvent is removed.

According to the separating method of the present invention, the D isomer and the L isomer can readily be separated from the amino acid derivative in which the D isomer and the L isomer are present in a mixture. Accordingly, the above separating method can suitably be used as an optical separating process in a method in which a non-separated amino acid derivative (that is, the present amino acid derivative in which the D isomer and the L isomer are present in a mixture) is obtained from a racemate or optically active basic amino acid by the chemical synthetic method described above or reaction using enzymes and microorganisms and in which the above non-separated amino acid derivative is optically separated to produce the D isomer or the L isomer having a high purity (a high optical purity).

Also, according to the separating method of the present invention, the respective amounts of the D isomer and the L isomer contained in the non-separated amino acid derivative can be determined in the state that they are separated from each other, and therefore it can suitably be used as an optical purity analytical method for a non-separated amino acid derivative having an unknown optical purity. In particular, the method carried out by the liquid chromatography described above among the separating method of the present invention not only is simple and has a high separating performance but also even if the D isomer and the L isomer are not isolated, use of an analytical curve makes it possible to determine the respective amounts at a high accuracy, and therefore it is an excellent analytical method for optical purity (an optical purity-measuring method).

Further, the analytical method for optical purity described above has the excellent characteristics described above and therefore can suitably be used, for example, as a method for process control in a method in which a non-separated amino acid derivative is obtained from a basic amino acid and in which the above non-separated amino acid derivative is subjected to optical separation (optical resolution) to thereby produce the D isomer or the L isomer having a high purity (a high optical purity). In this case, it is a matter of course that capable of being used as an optically separating method are, in addition to the separating method of the present invention, publicly known optical resolution methods such as a physically separating method making use of a crystal form of an optical isomer, a method using separation of a diastreomer as a principle, to be specific, a method in which a diastreomer is converted to a stable diastreomer (including a molecular complex) and in which it is then separated by operation such as crystal fractionation, chromatography and distillation, a method for selectively adsorbing and abstracting using a chiral adsorbent and a chiral solvent, an asymmetric conversion method and a method making use of asymmetric reaction.

The present invention shall be explained below in further details with reference to examples, but the present invention shall not be restricted by these examples.

EXAMPLE 1

An aqueous solution was prepared by mixing 10% (volume ratio) of acetonitrile (manufactured by Wako Pure Chemicals Industries, Ltd.) with a solution having a cyclodextrin concentration of 10 mM and a pH of 2 prepared by dissolving 11.35 g of β-cyclodextrin (manufactured by Tokyo Kasei Co., Ltd.) as a chiral selector in 1 L of a 0.1% phosphoric acid (volume ratio). Using this solution as a mobile phase and using a separation column Inertsil ODS-2 (manufactured by GL Science Co., Ltd.) filled with a stationary phase in which an octadecyl group was chemically bonded on the surface of a silica gel particle as a hydrophobic substance, N-(tert-butoxycarbonyl)-DL-alanine {(D isomer/L isomer) mole ratio=1/2} was injected into the above separating column to carry out high performance liquid chromatography, whereby a chromatogram was obtained.

The following apparatus and conditions for the high performance liquid chromatography were used in the present example.

Pump: 600E manufactured by Waters Co., Ltd.
Injector: U6K manufactured by Waters Co., Ltd.
Column oven: CTO10A manufactured by Shimadzu Mfg. Co., Ltd.
Detector: 991J manufactured by Waters Co., Ltd.
Mobile phase flow velocity: 1 ml/min
Column temperature: 30° C.
Column size: inner diameter 4.6 mm, length 250 mm
Detecting wavelength: 210 nm Based on the chromatogram obtained in the manner described above, the degree of optical isomer separation was evaluated by resolution (Rs) to find that Rs was 2.25, and it was confirmed that good separation was carried out.

This resolution (Rs) shows how well two peaks are separated and is a value defined by the following equation. It is shown that the larger this value is, the better the two peaks are separated, and it is shown that when Rs is 0, two peaks are not separated at all and that in the case of Rs>1, the two peaks reside in the state that they are completely separated as well in the base part:

$$Rs = 2(t_{R2} - t_{R1})/(W_1 + W_2)$$

wherein $t_{R1}$ shows a retention time of a peak 1 in a chromatogram obtained by separating a compound comprising two kinds of components; $t_{R2}$ shows a retention time of a peak 2; $W_1$ shows the base (time length) of the peak 1; $W_2$ shows the base (time length) of the peak 2.

EXAMPLE 2

N-(tert-butoxycarbonyl)-DL-alanine {(D isomer/L isomer) mole ratio=1/2} was separated by the same method as in Example 1, except that the separating column was changed to Inertsil C8 (manufactured by GL Science Co., Ltd.) filled with a stationary phase in which an octyl group was chemically bonded on the surface of a silica gel particle, and the degree of the separation was evaluated to find that Rs was 2.03 and that good separation could be carried out.

EXAMPLE 3

A proportion of acetonitrile was changed to 15% (volume ratio) to separate N-(tert-butoxycarbonyl)-DL-methionine {(D isomer/L isomer) mole ratio=1/2} by the same method as in Example 1, and the degree of the separation was evaluated to find that Rs was 1.46 and that good separation could be carried out.

EXAMPLE 4

N-(tert-butoxycarbonyl)-DL-leucine {(D isomer/L isomer) mole ratio=1/2} was separated by the same method as in Example 1, except that the separating column was changed to Inertsil PH (manufactured by GL Science Co., Ltd.) filled with a stationary phase in which a phenyl group was chemically bonded on the surface of silica gel and that a proportion of acetonitrile was changed to 15% (volume ratio), and the degree of the separation was evaluated to find that Rs was 2.18 and that good separation could be carried out.

EXAMPLE 5

Used as a mobile phase was a solution prepared by mixing 20% (volume ratio) of acetonitrile (manufactured by Wako Pure Chemicals Industries, Ltd.) with a solution having a cyclodextrin concentration of 30 mM prepared by dissolving 43.2 g of CAVASOL W7 HP (manufactured by Wacker Chemicals East Asia Co., Ltd.) which was cyclodextrin obtained by converting a hydroxyl group of β-cyclodextrin as a chiral selector to hydroxypropyl in 1 L of a 0.1% phosphoric acid (volume ratio), and Inertsil ODS-2 (manufactured by GL Science Co., Ltd.) was used as the column to separate N-(tert-butoxycarbonyl)-DL-phenylalanine {(D isomer/L isomer) mole ratio =1/2} by means of high performance liquid chromatography. The same apparatus as in Example 1 was used, and the sensitivity was good, so that a detecting wavelength of 254 nm was used, wherein Rs was 1.56, and good separation could be carried out.

EXAMPLE 6

Used as a mobile phase was a solution prepared by mixing 15% (volume ratio) of acetonitrile (manufactured by Wako Pure Chemicals Industries, Ltd.) with a solution having a cyclodextrin concentration of 10 mM prepared by dissolving 11.35 g of β-cyclodextrin (manufactured by Tokyo Kasei Co., Ltd.) in 1 L of a 10 mM triethylamine phosphate (manufactured by Tokyo Kasei Co., Ltd.) solution, and Inertsil ODS-2 (manufactured by GL Science Co., Ltd.) was used as the column to separate N-(tert-butoxycarbonyl)-DL-tryptophan {(D isomer/L isomer) mole ratio=1/2} by means of high performance liquid chromatography in the same manner as in Example 5 to find that Rs was 1.59.

EXAMPLE 7

Changed were triethylamine phosphate to tetrabutylammonium phosphate (manufactured by GL Science Co., Ltd.) and a proportion of acetonitrile to 10% (volume ratio), and the detecting wavelength was changed to 210 nm to separate N-(tert-butoxycarbonyl)-DL-proline {(D isomer/L isomer) mole ratio=1/2} in the same manner as in Example 6 to find that Rs was 1.91.

EXAMPLE 8

Used as a mobile phase was a solution prepared by mixing 15% (volume ratio) of acetonitrile (manufactured by Wako Pure Chemicals Industries, Ltd.) with a solution having a cyclodextrin concentration of 30 mM prepared by dissolving 43.2 g of CAVASOL W7 HP (manufactured by Wacker Chemicals East Asia Co., Ltd.) as a chiral selector in 1 L of a 10 mM tetrabutylammonium phosphate solution (manufactured by GL Science Co., Ltd.), and Inertsil ODS-2 (manufactured by GL Science Co., Ltd.) was used as the column to separate N-(tert-butoxycarbonyl)-DL-tyrosine {(D isomer/L isomer) mole ratio=1/2} by means of high performance liquid chromatography in the same manner as in Example 1. In detecting peaks, a detecting wavelength of 210 nm was used to monitor the absorbance. The result thereof showed that Rs was 1.96.

EXAMPLE 9

High performance liquid chromatography was carried out in the same manner as in Example 1, except that 10 mM sodium citrate was used as a pH controlling agent to control the pH to 2.8 and N-(tert-butoxycarbonyl)-L-tryptophan which was an amino acid derivative was used as the chiral selector and that N-benzyloxycarbonyl-DL-leucine {(D isomer/L isomer) mole ratio=1/2} was used as an object to be separated. In detecting peaks, a detecting wavelength of 254 nm was used to monitor the absorbance. The result thereof showed that Rs was 0.34 and that separation could be carried out.

EXAMPLE 10

High performance liquid chromatography was carried out in the same manner as in Example 1, except that 10 mM sodium citrate was used as a pH controlling agent to control the pH to 3.4 and benzyloxycarbonyl-L-alanine which was an amino acid derivative was used as the chiral selector and that N-benzoyl-DL-valine {(D isomer/L isomer) mole ratio=1/2} was used as an object to be separated. In detecting peaks, a detecting wavelength of 254 nm was used to monitor the absorbance. The result thereof showed that Rs was 0.08 and that separation could be carried out.

The results of Examples 1 to 10 are summarized in Table 1.

TABLE 1

| | Object to be separated | Hydrophobic substance (separating column) | pH | Composition of aqueous solution (mobile phase composition) | | | | |
| --- | --- | --- | --- | --- | --- | --- | --- | --- |
| | | | | pH controlling agent | Hydrophobic counter ion-forming compound | Chiral selector | Acetonitrile concentration | Resolution (Rs) |
| Example 1 | N-(tert-butoxycarbonyl)-DL-alanine | Inertsil ODS-2 | 2.0 | 0.1% Phosphoric acid | None | 10 mM β-cyclodextrin | 10% | 2.25 |
| Example 2 | N-(tert-butoxycarbonyl)-DL-alanine | Inertsil C8 | 2.0 | 0.1% Phosphoric acid | None | 10 mM β-cyclodextrin | 10% | 2.03 |
| Example 3 | N-(tert-butoxycarbonyl)-DL-methionine | Inertsil ODS-2 | 2.0 | 0.1% Phosphoric acid | None | 10 mM β-cyclodextrin | 15% | 1.46 |
| Example 4 | N-(tert-butoxycarbonyl)-DL-leucine | Inertsil PH | 2.0 | 0.1% Phosphoric acid | None | 10 mM β-cyclodextrin | 15% | 2.18 |
| Example 5 | N-(tert-butoxycarbonyl)-DL-phenylalanine | Inertsil ODS-2 | 2.0 | 0.1% Phosphoric acid | None | 30 mM CAVASOL W7 HP | 20% | 1.56 |

TABLE 1-continued

| | Object to be separated | Hydrophobic substance (separating column) | pH | pH controlling agent | Hydrophobic counter ion-forming compound | Chiral selector | Acetonitrile concentration | Resolution (Rs) |
|---|---|---|---|---|---|---|---|---|
| Example 6 | N-(tert-butoxycarbonyl)-DL-tryptophan | Inertsil ODS-2 | 7.0 | None | 10 mM Triethylamine phosphate | 10 mM β-cyclodextrin | 15% | 1.59 |
| Example 7 | N-(tert-butoxycarbonyl)-DL-proline | Inertsil ODS-2 | 7.5 | None | 10 mM Tetrabutyl-ammonium phosphate | 10 mM β-cyclodextrin | 10% | 1.91 |
| Example 8 | N-(tert-butoxycarbonyl)-DL-tyrosine | Inertsil ODS-2 | 7.5 | None | 10 mM Tetrabutyl-ammonium phosphate | 30 mM CAVASOL W7 HP | 15% | 1.96 |
| Example 9 | N-benzyl-oxycarbonyl-DL-leucine | Inertsil ODS-2 | 2.8 | 10 mM Sodium citrate | None | 20 mM N-(tert-butoxycarbonyl)-DL-tryptophan | 10% | 0.34 |
| Example 10 | N-benzoyl-DL-valine | Inertsil ODS-2 | 3.4 | 10 mM Sodium citrate | None | 30 mM Benziloxy-carbonyl-L-alanin | 10% | 0.08 |

EXAMPLE 11

A 5% solution 50 μl of N-(tert-butoxycarbonyl)-DL-alanine prepared by mixing in advance the D type and the L type in a proportion of each 50% was used as a sample to separate them in the same manner as in Example 1, and an area of the chromatographic peaks was calculated. As a result thereof, a proportion of the area was 50% of the D type to 50% of the L type. The proportion of the area was the same as the proportion in mixing, and it was confirmed that use of the separating method of the present invention made it possible to accurately measure the optical purity by a simple operation.

Further, the effluents eluted from the column which corresponded to the respective chromatographic peaks were fractioned respectively. The effluent of the chromatographic peak eluted earlier was designated as an effluent 1, and the effluent of the chromatographic peak eluted later was designated as an effluent 2. Next, the effluent 1 and the effluent 2 were subjected to the following operation to measure an optical purity of the amino acid derivative contained in the respective effluents.

That is, a separating funnel was charged with the effluent described above and chloroform of almost the same volume of the effluent and shaken for one minute, and then it was left standing still. Thereafter, the chloroform layer was taken out into a Kjehldhl flask, and chloroform was removed by distillation under reduced pressure to obtain a white solid matter. Then, 1 ml of dioxane was added to the above white solid matter to dissolve again the white solid matter described above, and insoluble matters were removed by filtering. A 4N hydrogen chloride dioxane solution was added to the dioxane solution of the filtrate and mixed to carry out deblocking (substitution of tert-butoxycarbonyl with a hydrogen atom). Then, the solution was left standing for 12 hours, and the resulting amino acid hydrochloride was recovered by filtering and sufficiently dried under vacuum, followed by dissolving it in 0.1 ml of a 10 mM phosphoric acid buffer solution (pH 7.0). Then, 10 μl of the phosphoric acid buffer solution thus obtained was separated and analyzed by means of a commercial column for separating amino acid optical isomers (CHIRALPAK WE manufactured by Daicel Chemical Industry Co., Ltd.) on the following conditions.

Analytical conditions:
Pump: 600E manufactured by Waters Co., Ltd.
Injector: U6K manufactured by Waters Co., Ltd.
Column oven: CTO10A manufactured by Shimadzu Mfg. Co., Ltd.
Detector: 991J manufactured by Waters Co., Ltd.
Mobile phase composition: 0.25 mM copper sulfate aqueous solution
Mobile phase flow velocity: 0.6 ml/min
Column temperature: 50° C.
Column size: inner diameter 4.6 mm, length 250 mm
Detecting wavelength: 210 nm As a result thereof, it was confirmed that the white solid matters described above obtained respectively from the effluent 1 and the effluent 2 were N-(tert-butoxycarbonyl)-alanine of a 100% D type and N-(tert-butoxycarbonyl)-alanine of a 100% L type.

COMPARATIVE EXAMPLE 1

N-(tert-butoxycarbonyl)-DL-alanine was separated in the same manner as in Example 1, except that β-cyclodextrin which was the chiral selector was not added to the mobile phase. However, Rs was 0, and the D type was not separated at all from the L type.

COMPARATIVE EXAMPLES 2 to 4

N-(tert-butoxycarbonyl)-DL-alanine was separated in the same manner as in Example 1, except that a pH of the mobile phase was changed to a value larger than 3.5 as shown in Table 2 using a sodium acetate buffer solution having a concentration of 10 mM. The results thereof are shown in Table 2. In all case, Rs was 0, and the D type was not separated at all from the L type.

TABLE 2

| | Object to be separated | Hydrophobic substance (separating column) | pH | pH controlling agent | Hydrophobic counter ion-forming compound | Chiral selector | Acetonitrile concentration | Resolution (Rs) |
|---|---|---|---|---|---|---|---|---|
| Comparative Example 1 | N-(tert-butoxycarbonyl)-DL-alanine | Inertsil ODS-2 | 2 | 0.1% Phosphoric acid | None | None | 10% | 0 |
| Comparative Example 2 | N-(tert-butoxycarbonyl)-DL-alanine | Inertsil ODS-2 | 3.6 | 10 mM Sodium acetate | None | 10 mM β-cyclodextrin | 10% | 0 |
| Comparative Example 3 | N-(tert-butoxycarbonyl)-DL-alanine | Inertsil ODS-2 | 3.7 | 10 mM Sodium acetate | None | 10 mM β-cyclodextrin | 10% | 0 |
| Comparative Example 4 | N-(tert-butoxycarbonyl)-DL-alanine | Inertsil ODS-2 | 4.1 | 10 mM Sodium acetate | None | 10 mM β-cyclodextrin | 10% | 0 |
| Comparative Example 5 | N-(tert-butoxycarbonyl)-DL-tryptophan | Inertsil ODS-2 | 5.4 | 10 mM Sodium acetate | None | 10 mM β-cyclodextrin | 10% | 0 |
| Comparative Example 6 | N-(tert-butoxycarbonyl)-DL-tryptophan | Inertsil ODS-2 | 7 | 10 mM Potassium dihydrogen phosphate-disodium hydrogenphosphate | None | 10 mM β-cyclodextrin | 15% | 0 |

COMPARATIVE EXAMPLE 5

N-(tert-butoxycarbonyl)-DL-tryptophan was separated and analyzed in the same manner as in Example 6 except that used was the mobile phase to which triethylamine being a compound producing a hydrophobic counter ion was not added. The results thereof are shown in Table 2. As shown in Table 2, Rs was 0, and the D type could not be separated at all from the L type.

COMPARATIVE EXAMPLE 6

In Comparative Example 5, a phosphoric acid buffer solution (prepared by mixing potassium dihydrogenphosphate and disodium hydrogenphosphate) was added as a controlling agent for pH, and the pH was controlled to 7 which was the same as in Example 6 to carry out the separation. However, Rs was still 0, and the D type could not be separated at all from the L type.

COMPARATIVE EXAMPLE 7

Using as a filler, Sumichiral OA7000 which was a commercial column for separating optical isomers (a separating column using a carrier obtained by fixing β-cyclodextrin on the surface of a silica gel particle) and using a 20 mM $KH_2PO_4$ aqueous solution (pH 2.5) containing 20 % of acetonitrile as a mobile phase, N-(tert-butoxycarbonyl)-DL-phenylalanine {(D isomer/L isomer) mole ratio=1/2} was injected thereinto to carry out high performance liquid chromatography. The following apparatus and conditions were used in this case.

Pump 600E manufactured by Waters Co., Ltd.
Injector U6K manufactured by Waters Co., Ltd.
Column oven: CTO10A manufactured by Shimadzu Mfg. Co., Ltd.
Detector: 991J manufactured by Waters Co., Ltd.
Mobile phase flow velocity: 1 ml/min
Column temperature: 30° C.
Column size: inner diameter 4.6 mm, length 250 mm
Detecting wavelength: 210 nm The resolution of the chromatogram obtained was examined to find that Rs was 0 and that the D type was not separated at all from the L type.

EXAMPLE 12

N-(tert-butoxycarbonyl)-DL-alanine {(D isomer/L isomer) mole ratio=1/2} of a racemic body was dissolved in 10 ml of an aqueous solution which contained 10 mM of β-cyclodextrin as the chiral selector and in which a pH was adjusted to 2 with phosphoric acid so that a concentration of 100 mM was obtained. This aqueous solution and 10 ml of chloroform which was a liquid hydrophobic substance were put into a separating funnel, and it was shaken for 3 minutes and then left standing still. Thereafter, 5 ml of the hydrophobic substance was taken out and distilled under reduced pressure to remove chloroform, whereby a white solid matter was obtained. Then, the white solid matter thus obtained was dissolved in 10 ml of an aqueous solution which contained 10 mM of β-cyclodextrin as the chiral selector and in which a pH was adjusted to 2 with phosphoric acid so that a concentration of 100 mM was obtained, and the above solution was brought into contact with 10 ml of chloroform in the same manner as described above. Then, the chloroform layer was separated, and chloroform was removed to recover the white solid matter. This white solid matter was repeatedly subjected to the separation operation so that the total separation operation frequency reached five times to obtain a white solid matter. The white solid matter finally obtained was subjected to deblocking in the same manner as in the white solid matter obtained from the effluent 1 in Example 11, and then a commercial column for separating amino acid optical isomers was used to carry out high performance liquid chromatography. The result thereof showed that a (D isomer/L isomer) mole ratio was 0.53.

INDUSTRIAL APPLICABILITY

The present invention provides a novel method for separating the D isomer and the L isomer from the amino acid derivative in which a D isomer and an L isomer are present in a mixture and which has a specific substituent. It has a high separating capacity as compared with those of conventional separating methods and makes it possible to separate readily and completely the D isomer from the L isomer by adopting, for example, the method described above carried out by high performance liquid chromatography.

Accordingly, the separating method of the present invention not only can suitably be applied as an optically separating method used when the amino acid derivative having a high optical purity is produced from the amino acid derivative having a low optical activity by optical resolution but also can suitably be applied as a method for measuring an optical purity. Further, it can be applied to process control in producing the amino acid derivative having a high optical purity using a conventional optical resolving method. Thus, the present invention can be used for producing amino acid derivatives, medicines and the like.

The invention claimed is:

1. A method for separating respective optical isomers from a mixture containing a pair of optical isomers of an amino acid derivative, in which one of hydrogen atoms of an amino group or an imino group of amino acid having at least one asymmetric carbon is N-substituted with an organic carbonyl group to form an N-substituted amino acid derivative, said method comprising:
   (A) preparing the above mixture,
   (B) mixing the above mixture with a hydrophilic compound having a different affinity to the respective optical isomers contained therein in an aqueous solution to form an aqueous solution or aqueous suspension containing the complex,
   (C) subjecting the aqueous solution or aqueous suspension containing the above complex to:
      (i) a condition whereby the pH is 3.5 or lower, or
      (ii) the coexistence thereof with a compound having a group which can be a counter ion for an ion originating in a charging group of the above amino acid derivative and a hydrophobic atomic group,
   whereby a difference in hydrophobicity is brought about between complexes of the respective optical isomers, and
   (D) separating the complexes of the respective optical isomers from each other by making use of such difference in the hydrophobicity by bringing the respective optical isomers into contact with a hydrophobic substance selected from the group consisting of a hydrophobic organic solvent or a solid fine particle having a hydrophobic surface, and
   further wherein:
   said N-substituted amino acid derivative is represented by Formula (I):

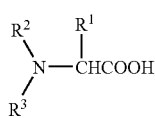

wherein $R^1$ represents a non-substituted or substituted $C_{1-6}$ alkyl group, and the substituent used when substituted is selected from the group consisting of hydroxy, mercapto, methylthio, amino, mono- or dimethylamino, $C_{1-6}$ alkylcarbonylamino, $C_{1-6}$ alkyloxycarbonyl, amidinoamino, carboxy, $C_{1-6}$ alkyloxycarbonyl, carbamoyl, non-substituted or substituted phenyl, wherein the substituents in the case of substituted phenyl are the same or different and can be 1 to 3 halogen atoms, hydroxy, mercapto, methyl, trifluoromethyl or amino;
one of $R^2$ and $R^3$ is a hydrogen atom, and the other represents alkoxycarbonyl, aralkyloxycarbonyl, aryloxycarbonyl, alkenyloxycarbonyl or acyl,
said hydrophilic compound is selected from the group consisting of polysaccharides and derivatives thereof and optically active compounds of amino acid and derivatives thereof, and
said hydrophobic atomic group is an alkyl group having 1 to 22 carbon atoms, which may have a substituent selected from the group consisting of hydroxyl group, nitro group and halogen atom, or an aryl group, which may have a substituent selected from the group consisting of hydroxyl group, nitro group and halogen atom.

2. The method as described in claim 1, wherein the N-substituted amino acid derivative originates in amino acid selected from the group consisting of alanine, proline, leucine, isoleucine, valine, phenylalanine, tyrosine, serine, methionine, glutamine, glutamic acid and lysine.

3. The method as described in claim 1, wherein the alkoxycarbonyl is $C_{1-9}$ alkyloxycarbonyl; the aralkyloxycarbonyl is non-substituted or substituted phenyl-$C_{1-4}$ alkyleneoxycarbonyl or 9-fluorenyl-$C_{1-4}$ alkyleneoxycarbonyl, and the substituent used when substituted may be the same or different and is 1 to 3 methyls, nitros, methoxys or halogens; the aryloxycarbonyl is non-substituted or substituted phenyloxycarbonyl, and the substituent used when substituted is the same as defined in the "substituted phenyl-"; the alkenyloxycarbonyl is $C_{3-9}$ alkenyloxycarbonyl; and the acyl is formyl, $C_{1-6}$ alkylcarbonyl or benzoyl.

4. The method as described in claim 1, wherein the polysaccharides and derivatives thereof of said hydrophilic compound are cyclodextrin and derivatives thereof.

5. The method as described in claim 1, wherein the optically active compounds of the amino acid and the derivative thereof are selected from L- or D-phenylalanine, L- or D-tryptophan and L- or D-leucine, and the derivative thereof is selected from N-(tert-butoxycarbonyl) compounds corresponding to the respective optically active compounds.

6. The method as described in claim 1, wherein step (C) is carried out under the condition that the pH in (i) is 3.5 or lower.

7. The method as described in claim 1, wherein step (C) is carried out under the coexistence of the compound having a group which can be a counter ion and a hydrophobic atomic group in (ii), and the above compound has a non-substituted or substituted $C_{1-22}$ alkyl group or a non-substituted or substituted aryl group as the hydrophobic atomic group and has a quaternary ammonium group as the group which can be a counter ion.

8. The method as described in claim 1, wherein the hydrophobic substance is a stationary phase having a hydrophobic surface.

9. A production process for producing an optically active amino acid or derivative thereof, said process comprising the method of claim 1, further wherein the preparation of a mixture containing a pair of optical isomers of an N-substituted amino acid derivative in the step (A) is carried out by converting a nitrogen atom of an amino group or an imino group of the respective optical isomers contained in a pair of an optical isomer mixture of amino acid having at least one asymmetric carbon into organic carbonyl, and the production process further comprises a step for obtaining any one of the optical isomers obtained in step (D) and deblocking, if necessary, the N-organic carbonyl group.

10. The production process as described in claim 9, wherein the converting a nitrogen atom of an amino group or an imino group of the respective optical isomers into organic carbonyl is carried out by reacting an amino acid represented by Formula (I-a):

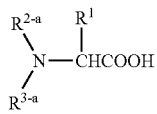

wherein:
R$^1$ is the same as the definition in Formula (I) described in claim 1, and
R$^{2-a}$ and R$^{3-a}$ are independently a hydrogen atom or can represent propane-1,3-diyl, 2-hydroxypropane-1,3-diyl or 1-hydroxypropane-1,3-diyl which can form a 5-membered ring via a nitrogen atom they are bonded to by combining any one of them with R$^1$, with an active ester of an acid in a solvent exerting no adverse effect on the reaction, wherein the active ester of an acid is represented by Formula (II):

$$A\text{---}COOH \qquad (II)$$

wherein A represents alkoxy, aralkyloxy, aryloxy, alkenyloxy or alkyl or ary.

11. An analytical method for analyzing optical purity of a mixture of a pair of optical isomers of an amino acid derivative, said analytical method comprising the method of claim 1, further comprising a step for quantifying any one or both of the complexes of the respective optical isomers which are separated from each other in step (D).

12. The analytical method as described in claim 11, wherein separation in step (D) is carried out by bringing a stationary phase having a hydrophobic surface into contact with the respective optical isomers.

13. A production process for an optically active amino acid having a high optical purity, comprising monitoring a production process for an optically active amino acid by the analytical method as described in claim 11.

14. A production process for an optically active amino acid having a high optical purity, comprising monitoring a production process for an optically active amino acid by the analytical method as described in claim 12.

* * * * *